(12) United States Patent
Epple

(10) Patent No.: US 11,697,016 B2
(45) Date of Patent: Jul. 11, 2023

(54) CATHETER PUMP HAVING A PUMP HEAD FOR INTRODUCING INTO THE ARTERIAL VASCULATURE

(71) Applicant: CardioBridge GmbH, Hechingen (DE)

(72) Inventor: Klaus Epple, Rangendingen (DE)

(73) Assignee: CardioBridge GmbH, Hechingen (DE)

( * ) Notice: Subject to any disclaimer, the term of this patent is extended or adjusted under 35 U.S.C. 154(b) by 1007 days.

(21) Appl. No.: 16/484,811

(22) PCT Filed: Feb. 8, 2018

(86) PCT No.: PCT/EP2018/053125
§ 371 (c)(1),
(2) Date: Aug. 8, 2019

(87) PCT Pub. No.: WO2018/146173
PCT Pub. Date: Aug. 16, 2018

(65) Prior Publication Data
US 2020/0023109 A1    Jan. 23, 2020

(30) Foreign Application Priority Data

Feb. 13, 2017   (DE) ..................... 10 2017 102 828.5

(51) Int. Cl.
*A61M 60/135*   (2021.01)
*A61M 60/148*   (2021.01)
(Continued)

(52) U.S. Cl.
CPC .......... *A61M 60/135* (2021.01); *A61M 60/13* (2021.01); *A61M 60/139* (2021.01);
(Continued)

(58) Field of Classification Search
CPC .............. A61M 60/135; A61M 60/237; A61M 60/859; A61M 60/139; A61M 60/886;
(Continued)

(56) References Cited

U.S. PATENT DOCUMENTS

| 2011/0034874 A1 | 2/2011 | Reitan et al. |
| 2016/0022890 A1* | 1/2016 | Schwammenthal ........................ A61M 60/833 600/16 |

FOREIGN PATENT DOCUMENTS

| DE | 20 2009 018 145 U1 | 6/2011 |
| EP | 0 768 900 B1 | 3/2002 |

(Continued)

*Primary Examiner* — Tammie K Marlen
(74) *Attorney, Agent, or Firm* — Aslan Law, P.C.

(57) ABSTRACT

A catheter pump having a rotor shaft rotatably arranged in the inner catheter for driving an expandable conveyor element provided at the pump head. The conveyor element is rotatably mounted between a. distal hearing point and a proximal bearing point, wherein the outer catheter has a sleeve section on the distal end thereof surrounding the proximal bearing point, and wherein the proximal bearing point can be moved in the axial direction relative to the sleeve section in order to expand the conveyor element, wherein the proximal bearing point comprises a bearing receiver having a rotational bearing point for a rotary head rotationally fixed to the distal end of the rotor shaft, and a force application point at an axial distance to same for a force application section provided at the distal end of the inner catheter for axially moving the proximal bearing points relative to the sleeve section.

16 Claims, 3 Drawing Sheets

(51) Int. Cl.
    A61M 60/13      (2021.01)
    A61M 60/237     (2021.01)
    A61M 60/808     (2021.01)
    A61M 60/857     (2021.01)
    A61M 60/859     (2021.01)
    A61M 60/139     (2021.01)
    F04D 29/046     (2006.01)
    A61M 60/825     (2021.01)
    A61M 60/403     (2021.01)
    A61M 60/886     (2021.01)
    A61M 60/38      (2021.01)
    A61M 60/408     (2021.01)

(52) U.S. Cl.
    CPC ........ *A61M 60/148* (2021.01); *A61M 60/237* (2021.01); *A61M 60/38* (2021.01); *A61M 60/403* (2021.01); *A61M 60/408* (2021.01); *A61M 60/808* (2021.01); *A61M 60/825* (2021.01); *A61M 60/857* (2021.01); *A61M 60/859* (2021.01); *A61M 60/886* (2021.01); *F04D 29/046* (2013.01); *A61M 2210/125* (2013.01); *A61M 2210/127* (2013.01)

(58) Field of Classification Search
    CPC .. A61M 60/148; A61M 60/13; A61M 60/825; A61M 60/38; A61M 60/808; A61M 60/408; A61M 60/857; A61M 60/403; A61M 2210/125; A61M 2210/127; F04D 29/046
    See application file for complete search history.

(56)            References Cited

FOREIGN PATENT DOCUMENTS

EP         2 308 422 B1    6/2013
    WO      WO 03/103745 A2   12/2003

* cited by examiner

CATHETER PUMP HAVING A PUMP HEAD FOR INTRODUCING INTO THE ARTERIAL VASCULATURE

CROSS-REFERENCE TO RELATED APPLICATIONS

This application claims priority to German Patent Application No. 10 2017 102 828.5 filed on Feb. 13, 2017, and to PCT Application No. PCT/EP2018/053125 filed on Feb. 8, 2018, the entire contents of which are hereby incorporated by reference.

The invention relates to a catheter pump having a pump head for introducing into the arterial vasculature such as the aorta or the heart, an outer catheter, an inner catheter arranged in the outer catheter, and a rotor shaft rotatably arranged in the inner catheter for driving an expandable conveyor element provided at the pump head, the conveyor element being rotatably mounted between a distal bearing point and a proximal bearing point, the outer catheter having, on the distal end thereof, a sleeve section surrounding the proximal bearing point, and it being possible to move the proximal bearing point in the axial direction relative to the sleeve section in order to expand the conveyor element.

Such catheter pumps are known, for example, from EP 2 308 422 B1. A rotor comprising fold-out propellers, as described in EP 768 900 B1, can be used as a rotating conveyor element, for example. It is also conceivable that differently shaped conveyor elements, for example a helically formed spiral, can be used.

Catheter pumps are inserted into the aorta of patients as a temporary circulatory support system, in particular when the natural heart is unable to provide the body with sufficient oxygenated blood. The conveyor element and the rotor shaft are operated at comparatively high speeds in the range of from 7,000 to 15,000 revolutions per minute. The pump head of the catheter pump can remain in the aorta for several days, in particular after surgery.

The problem addressed by the present invention is that of advantageously designing the proximal bearing point of the catheter pump mentioned at the outset.

This problem is solved by a catheter pump having the features of claim 1. The invention thus provides that the proximal bearing point, i.e. the bearing point which lies between the catheters and the other, distal bearing point in the axial direction, comprises a bearing receiver which has a rotational bearing point for a rotary head rotationally fixed to the distal end of the rotor shaft, and a force application point at an axial distance therefrom for a force application section provided at the distal end of the inner catheter for axially moving the proximal bearing point relative to the sleeve section. By providing such a bearing receiver, which has the rotational bearing point and the force application point, several functions can be realized in a single component in the smallest space. On the one hand, the conveyor element, and in particular a rotor of the conveyor element, can be mounted in a rotationally secure manner in the rotational bearing point. On the other hand, a relative movement between the sleeve section of the outer catheter and the bearing receiver in order to expand the conveyor element can be carried out in a functionally reliable manner due to the provision of the force application point on the bearing receiver.

The sleeve section can be arranged integrally on the outer catheter or be formed thereby. It is also conceivable that the sleeve section may be formed as a separate component which is rigidly connected to the outer catheter.

For contracting or folding in the conveyor element, the sleeve section is moved relative to the proximal bearing point away from the distal bearing point in the axial direction.

Advantageously, the bearing receiver is sleeve-shaped. The rotational bearing point is formed by a first inner groove and the force application point is formed by a second inner groove. Overall, this allows a comparatively simple bearing receiver to be formed by the rotational bearing point and the force application point. The first inner groove can have comparatively flat chamfers, so that the rotary head can be stored in an appropriately convenient manner. In this case, the second inner groove can in particular be formed in such a way that a force application section formed as an annular collar can be received by the second inner groove in a functionally reliable manner.

In a particularly preferred embodiment, the bearing receiver comprises at least two bearing shells. Two half shells may be used to provide two bearing shells. The use of two or more bearing shells has the advantage that it is possible to mount the proximal bearing point in a simple manner.

For this purpose, the sleeve section is advantageously designed so that, in order to mount the proximal bearing point, initially the bearing shells are placed on the rotary head and the force application section in the radial direction and then the sleeve section is pushed over the bearing shells in the axial direction. This has the advantage that further mounting or fastening means can be omitted. The bearing shells are securely arranged in the sleeve section.

The bearing receiver and in particular the bearing shells can preferably have recesses on the radial outer side facing the sleeve section such that irrigation fluid flowing between the inner catheter and the outer catheter can flow between the bearing receiver, or bearing shells, and the inner wall of the sleeve section. The recesses are preferably formed in the bearing receiver or the bearing shells as channels extending in the axial direction. As a result, it is possible to ensure that irrigation fluid which is conveyed between the outer catheter and the inner catheter toward the pump head can pass through the proximal bearing point without the fluid having to pass through the rotational bearing point.

Furthermore, it is conceivable according to the invention that a storage chamber adjoins the distal end of the bearing receiver, in which chamber irrigation fluid collects during operation and from which the irrigation fluid is conducted further to the distal bearing point, into the aorta and/or back through the inner catheter. As a result, on the one hand, the distal bearing point can also be supplied with appropriate irrigation fluid. On the other hand, a portion of the irrigation fluid, which may be in the range of one third of the introduced irrigation fluid, may be removed past the rotary head through the rotational bearing point and back through the inner catheter. It is thereby possible that the rotational bearing point can also be sufficiently irrigated and lubricated with appropriate irrigation fluid. The irrigation fluid passing through the rotational bearing point is thus conveyed back through the inner catheter or through a lumen between the inner catheter and the rotor shaft, so that potential bearing wear does not reach the bloodstream of the patient if possible.

The force application section is advantageously arranged on a bushing which is fixedly arranged on the distal end of the inner catheter. The bushing can surround the inner catheter in the radial direction. The force application section can be designed in particular as an annular collar which projects in the radial direction and engages in the second inner groove of the bearing receiver. In this way, a secure movement coupling acting in the axial direction between the inner catheter or bushing and the bearing receiver or bearing shells can be provided.

The bushing can in turn have a collar section at a distance from the force application section on the side facing away from the rotational bearing point. This collar section can be used as an axial stop against the outer catheter, or against a spacer sleeve provided between the bushing and the outer catheter.

It is advantageous if the spacer sleeve has openings extending in the radial direction for the passage of irrigation fluid. It can thereby be ensured that irrigation fluid which is conveyed between the into the catheter and the outer catheter toward the proximal bearing point can also be conducted between the lower section and the spacer sleeve when the spacer sleeve is completely in contact with the collar section.

Further details and advantageous designs of the invention can be found in the following description, on the basis of which one embodiment of the invention is explained and described in more detail.

Figure 1:
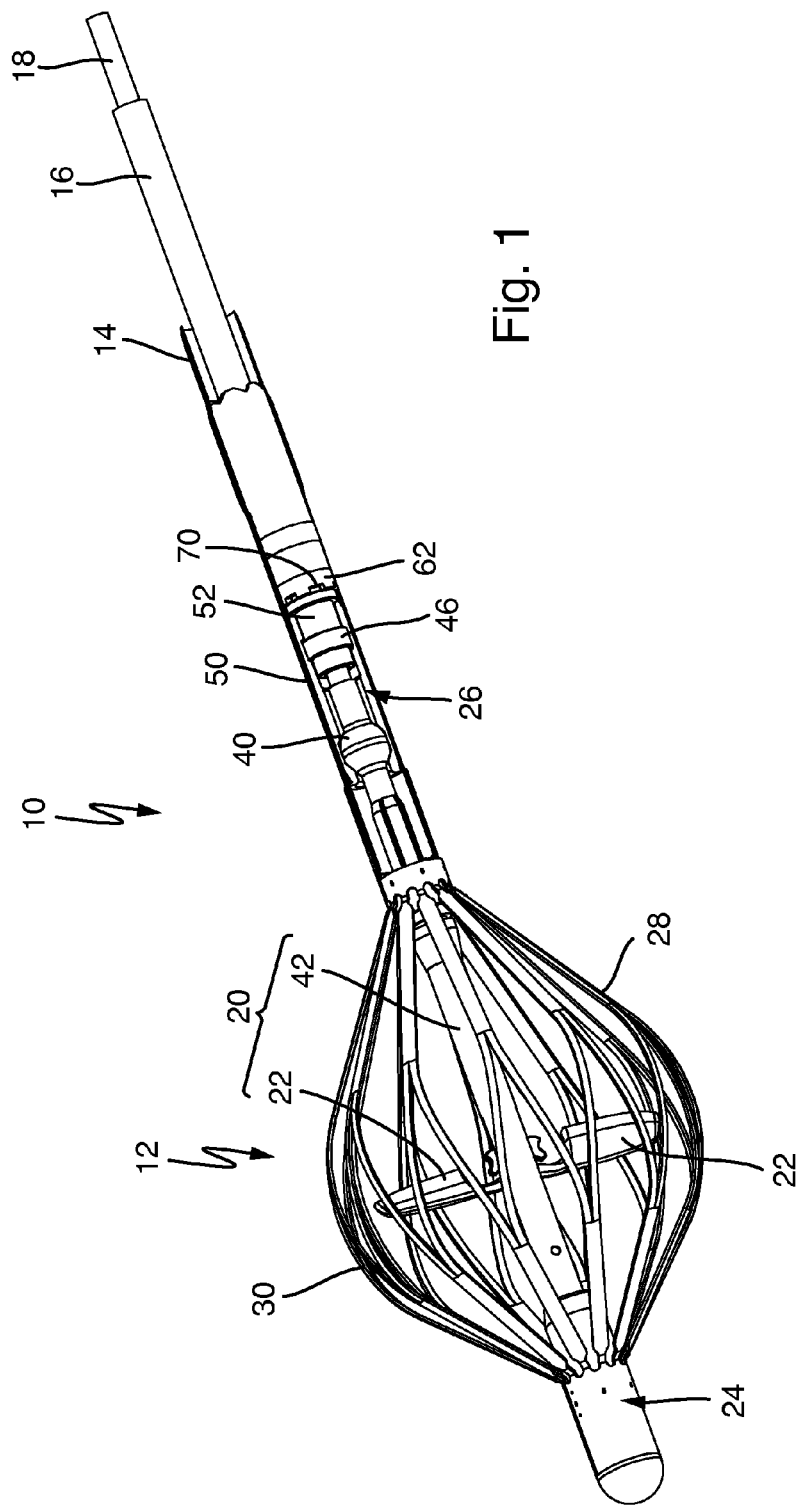
FIG. 1 is a perspective view of a pump head of a catheter pump according to the invention with a partially cut-away proximal bearing point.

The catheter pump 10 shown in FIG. 1 comprises a pump head 12 for introducing into the aorta or the heart of a patient. The pump 10 comprises an outer catheter 14, an inner catheter 16 and a rotor shaft 18 rotatably arranged in the inner catheter 16. A conveyor element 20 shown expanded in FIG. 1 can be driven in the form of a rotor 42 with propellers 22 by means of the rotor shaft 18. The propellers 22 are arranged between a distal bearing point 24 and a proximal bearing point 26 on the rotor 42. The conveyor element 20 or propellers 22 are surrounded by a cage 28 which provides various filaments 30. In the expanded state, which is shown in FIG. 1, the cage 28 is formed like a bulb, so that the propellers 22 can rotate freely within the cage 28. For introducing the pump head 12 into the aorta, the pump head 12 is not expanded, but is in a collapsed or folded state. In this collapsed state, the propellers 22 are close to the axis of rotation of the rotor 42, and the filaments 30 of the cage 28 are in a position parallel to the axis of rotation of the rotor 42.

Figure 2:
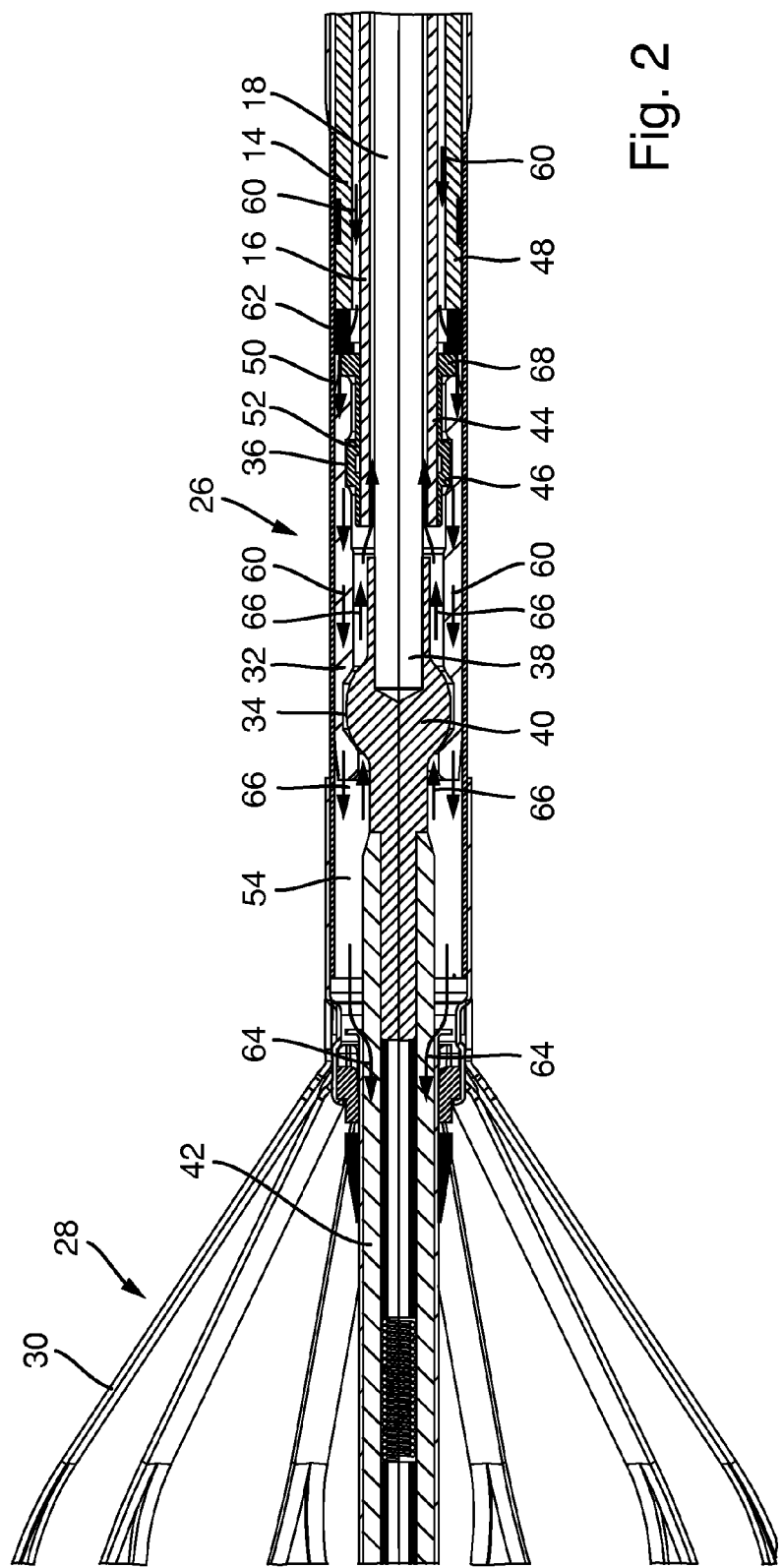
FIG. 2 is a longitudinal section through the proximal bearing point shown in FIG. 1.

As is clear from the section according to FIG. 2, the proximal bearing point 26 has a bearing receiver 32, which comprises a rotational bearing point 34 and a force application point 36. The rotational bearing point 34 and the force application point 36 are each formed in the sleeve-like bearing receiver 32 as circumferential inner grooves.

A rotary head 40, preferably a ball head, which is rotationally fixed to the distal end 38 of the rotor shaft 18, is rotatably mounted in the rotational bearing point 34. The rotor 42 comprising the propellers 22 is driven by means of the rotary head 40. The rotor shaft 18 is in turn driven in operation at its proximal end (not shown) by means of a drive.

A force application section 46 is provided in the force application point 36. The force application section 46 is formed by an annular collar, which is provided on a bushing 52 rigidly connected to the inner catheter 16. The annular collar engages positively in the force application point 36 which is formed by the bearing receiver 32 and is designed as a circumferential inner groove.

The bearing receiver 32 is in turn accommodated in a sleeve section 50 which is arranged at the distal end 48 of the outer catheter 14 and can be moved in the axial direction relative to the bearing receiver 32, and thus relative to the inner catheter 16.

By means of the described arrangement, by axially moving the outer catheter 14 relative to the inner catheter 16 and thus relative to the bearing receiver 32 that is movement-coupled with the inner catheter 16, the sleeve section 50 can be displaced from the distal position shown in FIG. 2, in which the conveyor element 20 is expanded, to the right into a proximal position, as a result of which the propellers 22 are folded and the cage 28 collapses.

In the distal position of the sleeve section 50 shown in FIG. 2, there is a storage chamber 54 adjoining the distal end of the bearing receiver 32. This storage chamber 54 results from the fact that the sleeve section 50 is displaced axially in the distal direction when the conveyor element 20 expands. In the proximal position of the sleeve section 50, that is to say in the case of a collapsed conveyor element 20, the bearing receiver 32 is located in the storage chamber 54.

Figure 3:
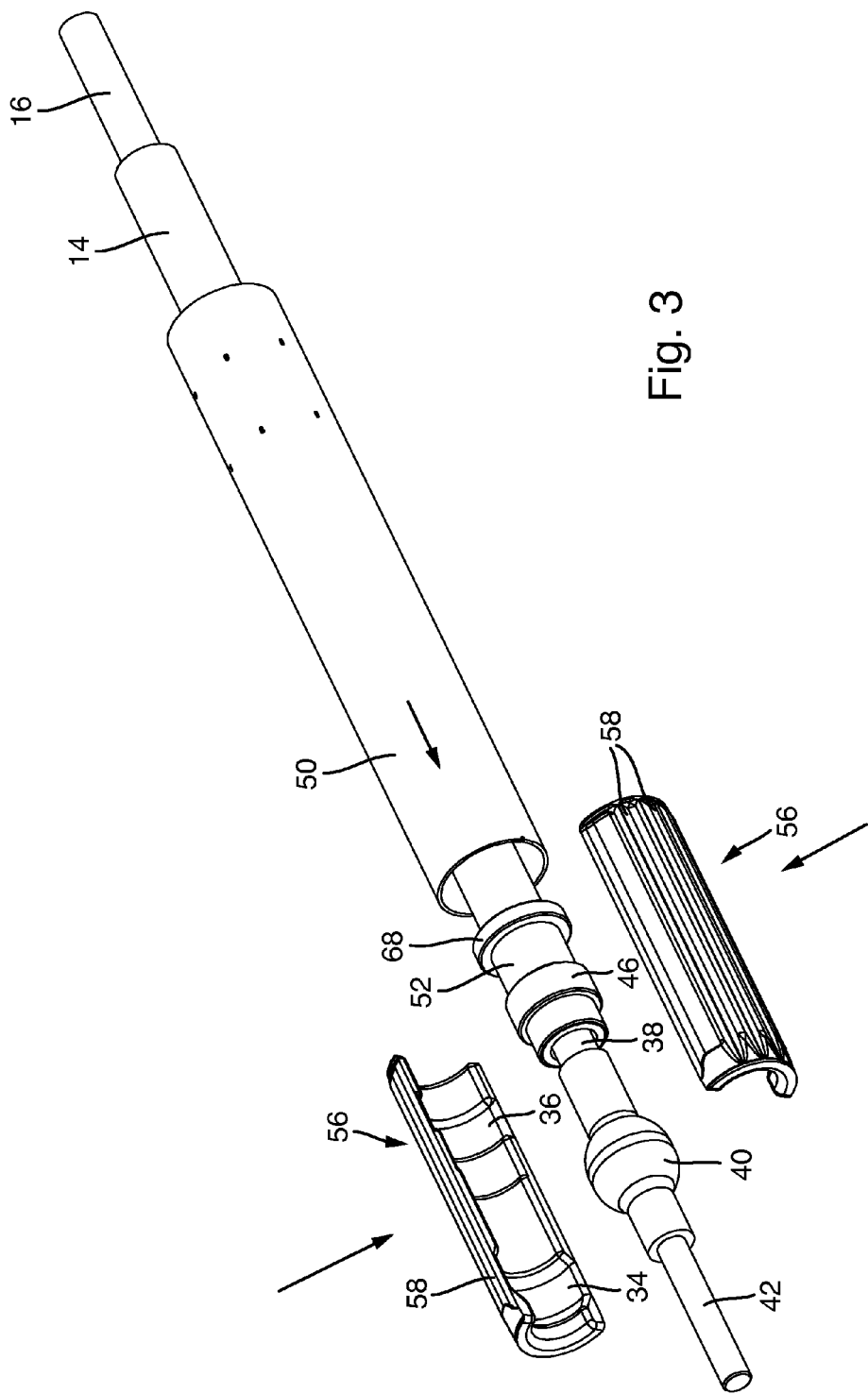
FIG. 3 shows the bearing point shown in FIG. 2 before mounting.

As is clear from FIG. 3, the bearing receiver 32 consists of two bearing shells 56. In order to mount the proximal bearing point 26, first the two bearing shells 56 are placed on the rotary head 40 and the force application section 46 in the radial direction. Subsequently, the sleeve section 50 is pushed over the bearing shell 56 in the axial direction. This has the advantage that a mounting or securing of the bearing shells 56 can be carried out without further components or securing means. With this arrangement, the requirements for this mounting can be realized in the smallest space.

On the side facing away from the rotational bearing point 34, the bushing 52 has a collar section 68 which is at a distance from the force application section 46. The collar section 68, together with a spacer sleeve 62, can act as an axial stop, and thus limit the axial displacement path of the sleeve section 50.

As is also clear from FIG. 3, the bearing shells 56 have recesses 58 on their radially outer side in the form of channels extending in the axial direction. During operation of the catheter pump 10, irrigation fluid flowing between the inner catheter 16 and the outer catheter 14, which fluid is indicated by the arrow 60 in FIG. 2 and passes through a spacer sleeve 62, can flow between the bearing shells 56 and the inner wall of the sleeve section 50 into the storage chamber 54. The irrigation fluid, which is pumped under pressure between the inner catheter 16 and the outer catheter 14, thereby collects in the storage chamber 54, so that a large portion of the irrigation fluid in the intake does not come into contact with the rotary head 40 or the rotational bearing point 34. From the storage chamber 54, the irrigation fluid can then be transported, as indicated by the arrows 64, via corresponding openings (not shown in the drawings), to the distal bearing point 24 for supplying the bearing point 24. Another portion of the irrigation fluid can escape from the storage chamber 54 via a rotational decoupling, which is not further identified in the drawings, into the aorta. A third portion, about one third of the irrigation fluid, can flow from the storage chamber 54, as indicated by the arrows 66, through the rotational bearing point 34 for irrigation and lubrication thereof, and be removed between the inner catheter 16 and the rotor shaft 18 toward the proximal end of the outer catheter 14. In this way, both the rotary head 40 and the entire rotor shaft 18 can be supplied with sufficient irrigation and lubrication, the proportion of irrigation fluid flowing through the bearing receiver 32 not reaching the aorta of the patient.

On the side facing away from the rotational bearing point 34, the bushing 52 has a collar section 68 which is at a distance from the force application section 46. Together with the spacer sleeve 62, this can act as an axial stop. So that the irrigation fluid can be conducted unhindered between the bushing 52 and the spacer sleeve 62, the spacer sleeve 62, as shown in FIG. 1, comprises axial openings 70 which remain open even when the spacer sleeve 62 rests against the collar section 68 of the bushing 52.

Owing to the described design of the proximal bearing point 26, a simple yet reliable mounting of the bearing point 26 with the two bearing shells 56 can take place, while nevertheless ensuring an axial movement of the proximal bearing point 26 relative to the sleeve section 50 in order to expand the conveyor element 20.

The invention claimed is:

1. A Catheter pump having a pump head for introducing into an arterial vasculature,
    an outer catheter,
    an inner catheter arranged in the outer catheter, wherein the inner catheter comprises a force application section at a distal end of the inner catheter, and
    a rotor shaft rotatably arranged in the inner catheter for driving an expandable conveyor element provided at the pump head, wherein
    the rotor shaft comprises a rotary head rotationally fixed to a distal end of the rotor shaft,
    the expandable conveyor element being rotatably mounted at a distal bearing and at a proximal bearing,
    the outer catheter has, on the distal end thereof; a sleeve section surrounding the proximal bearing,
    the proximal bearing is movable in the axial direction relative to the sleeve section for expanding the expandable conveyor element,
    the proximal bearing comprises a bearing receiver having a rotational bearing for the rotary head, wherein
    the bearing receiver comprises at least two bearing shells,
    a force application element at an axial distance from the proximal bearing receiver, and
    the force application section engages in the force application element for a movement coupling acting axially, so that by the force application section the force application element and thus also the proximal bearing can be moved relative to the sleeve section.

2. The Catheter pump according to claim 1, wherein the bearing receiver is cylindrical hollow-shaft-shaped and the rotational bearing is a first inner groove and the force application element is a second inner groove.

3. The Catheter pump according to claim 2, wherein the bearing receiver has recesses in the outer side facing the sleeve section such that irrigation fluid flowing between the inner catheter and the outer catheter can flow between the bearing receiver and an inner wall of the sleeve section.

4. The Catheter pump according to claim 2, wherein a storage chamber adjoins the distal end of the bearing receiver, in which chamber irrigation fluid collects during operation and from which the irrigation fluid is conducted further to the distal bearing, into the arterial vasculature and/or back through the inner catheter.

5. The Catheter pump according to claim 2, wherein the force application section is arranged on a bushing which is fixedly arranged on the distal end of the inner catheter.

6. The Catheter pump according to claim 1, wherein the sleeve seetion is such that, in order to mount the proximal bearing, first the bearing shells are placed on the rotary head and on the force application section in the radial direction and then the sleeve section is pushed over the bearing shells in the axial direction.

7. The Catheter pump according to claim 6, wherein the bearing receiver has recesses in the outer side facing the sleeve section such that irrigation fluid flowing between the inner catheter and the outer catheter can flow between the bearing receiver and an inner wall of the sleeve section.

8. The Catheter pump according to claim 7, wherein a storage chamber adjoins a distal end of the bearing receiver, in which chamber irrigation fluid collects during operation and from which the irrigation fluid is conducted further to the distal bearing, into the arterial vasculature and/or back through the inner catheter.

9. The Catheter pump according to claim 8, wherein the force application section is arranged on a bushing which is fixedly arranged on the distal end of the inner catheter.

10. The Catheter pump according to claim 9, wherein the bushing has a collar section at a distance from the force application section on the side facing away from the rotational bearing, which collar section forms an axial stop together with a spacer sleeve.

11. The Catheter pump according to claim 10, wherein the spacer sleeve has openings extending in the radial direction for the passage of irrigation fluid.

12. The Catheter pump according to claim 6, wherein a storage chamber adjoins the distal end of the bearing receiver, in which chamber irrigation fluid collects during operation and from which the irrigation fluid is conducted further to the distal bearing, into the arterial vasculature and/or back through the inner catheter.

13. The Catheter pump according to claim 1, wherein the bearing receiver has recesses in the outer side facing the sleeve section such that irrigation fluid flowing between the inner catheter and the outer catheter can flow between the bearing receiver and the inner wall of the sleeve section.

14. The Catheter pump according to claim 1, wherein a storage chamber adjoins the distal end of the bearing receiver, in which chamber irrigation fluid collects during operation and from which the irrigation fluid is conducted further to the distal bearing point, into the arterial vasculature and/or back through the inner catheter.

15. The Catheter pump according to claim 1, wherein the force application section is arranged on a bushing which is fixedly arranged on the distal end of the inner catheter.

16. A Catheter pump comprising:
    a pump head for introducing into an arterial vasculature,
    an outer catheter,
    an inner catheter arranged in the outer catheter, and
    a rotor shaft rotatably arranged in the inner catheter for driving an expandable conveyor element provided at the pump head, wherein
    the expandable conveyor element being rotatably mounted at a distal bearing and at a proximal bearing,
    the outer catheter has, on a distal end thereof; a sleeve section surrounding the proximal bearing,
    the proximal bearing is movable in an axial direction relative to the sleeve section for expanding the expandable conveyor element, the proximal bearing comprises a bearing receiver having a rotational bearing for a rotary head, wherein the inner catheter comprises a force application section, a force application element at an axial distance from the proximal bearing receiver for the force application section provided at a distal end of the inner catheter, wherein the bearing receiver comprises at least two bearing shells.

\* \* \* \* \*